United States Patent [19]

Becraft et al.

[11] Patent Number: 5,139,079

[45] Date of Patent: Aug. 18, 1992

[54] DYNAMIC MECHANICAL ANALYZER HAVING IMPROVED HEAT TRANSFER

[75] Inventors: Michael L. Becraft, Evansville; Don S. Mathew, New Harmony, both of Ind.

[73] Assignee: General Electric Company, Mt. Vernon, Ind.

[21] Appl. No.: 557,829

[22] Filed: Jul. 26, 1990

[51] Int. Cl.⁵ .......................................... F25B 29/00
[52] U.S. Cl. ................................ 165/61; 165/30; 165/48.1; 219/401
[58] Field of Search ............... 165/30, 48.1, 61, 64, 165/120, 903; 219/401

[56] References Cited

U.S. PATENT DOCUMENTS

| | | | |
|---|---|---|---|
| 3,536,132 | 10/1970 | Pecoraro et al. | 165/48.1 |
| 4,386,650 | 6/1983 | Moen | 165/30 |
| 4,572,283 | 2/1986 | Vanderschaaf | 165/61 |
| 4,609,035 | 9/1986 | Haslett et al. | 165/61 |
| 4,687,051 | 8/1987 | Zemp | 165/61 |
| 4,700,685 | 10/1987 | Miller | 219/401 |
| 4,911,230 | 3/1990 | Mayer et al. | 165/48.1 |

FOREIGN PATENT DOCUMENTS

| | | | |
|---|---|---|---|
| 676884 | 5/1939 | Fed. Rep. of Germany | 165/61 |
| 2056694 | 3/1981 | United Kingdom | 165/61 |

*Primary Examiner*—John Rivell
*Assistant Examiner*—L. R. Leo
*Attorney, Agent, or Firm*—Ronald Santucci; Martin Barancik

[57] ABSTRACT

The present invention provides for improved performance of a dynamic mechanical analyzer which measures mechanical and rheological properties of a material by reducing thermal lag in the material by modifying the radiative oven thereof to include a convective transfer device.

7 Claims, 3 Drawing Sheets

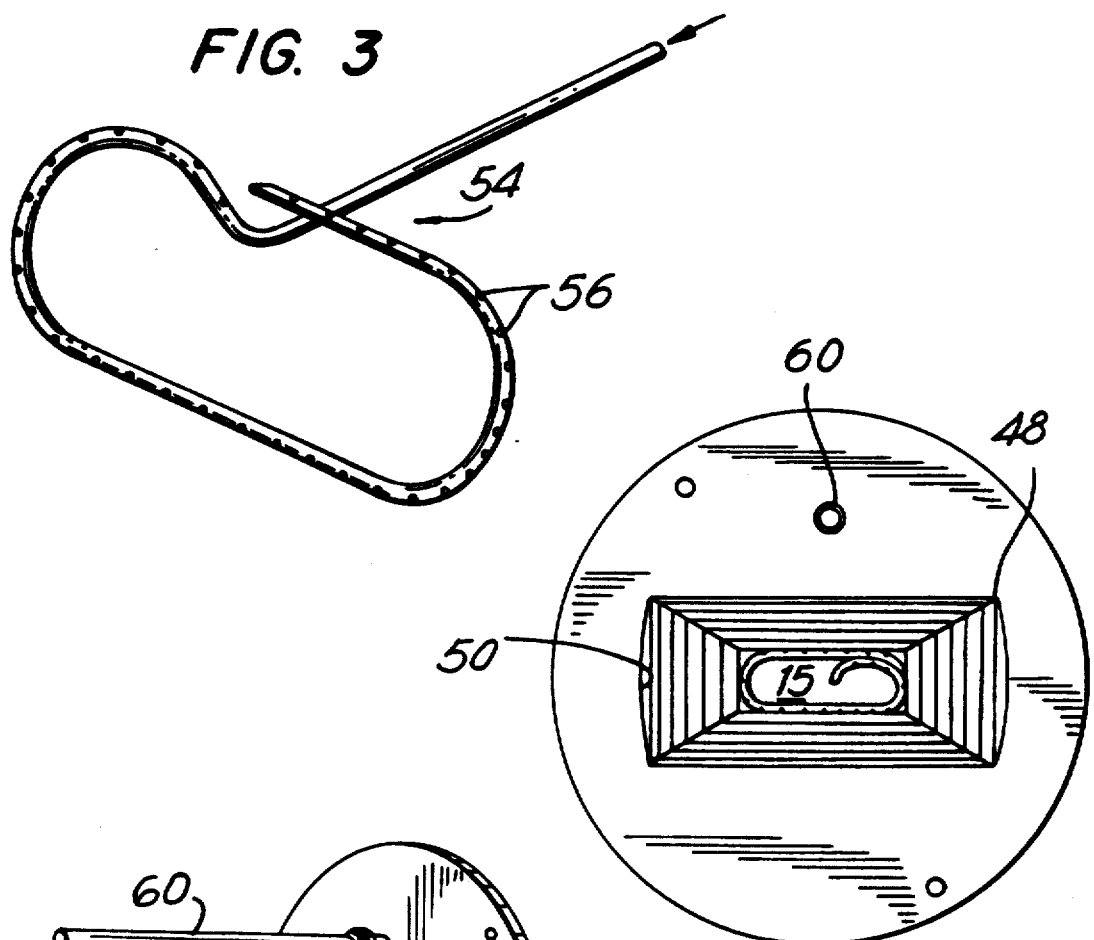
FIG. 3
FIG. 4
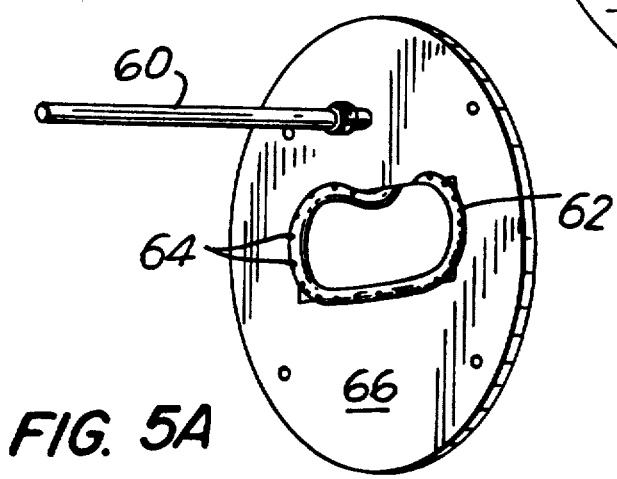
FIG. 5A
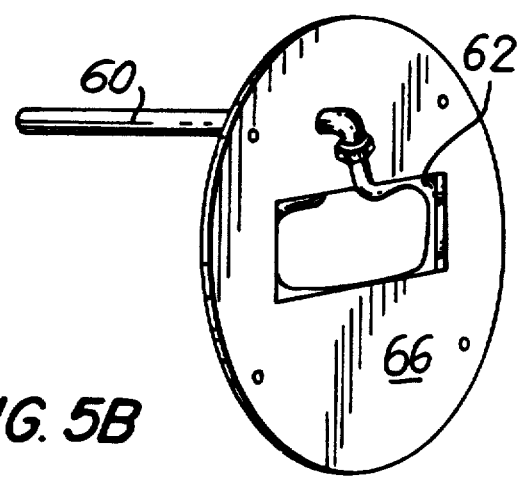
FIG. 5B

DYNAMIC MECHANICAL ANALYZER HAVING IMPROVED HEAT TRANSFER

BACKGROUND OF THE INVENTION

The present invention relates to improvements in the dynamic mechanical analysis of thermoplastic material.

Dynamic mechanical thermal analysis (sometimes referred to herein as "DMA") is a technique for measuring mechanical and rheological properties of thermoplastic materials in the solid state as a function of temperature. The technique involves subjecting a specimen, which typically is bar shaped, to bending or flexing at a given temperature and measuring the stiffness or resistance of the material to the imposed deformation. A series of such measurements over a range of temperatures provides information about the thermal behavior and mechanical properties of the material. Glass transitions and melting points are easily detected at temperatures where samples show softening and loss of stiffness.

An existing method for dynamic mechanical analysis utilizes molded bars, available for example in the form of Izod bars, for which little or no sample preparation is required. The thickness of Izod bars is, however, sufficient to create heat transfer limitations which significantly affect the speed of testing. As sample thickness increases, more time must be allowed for thermal equilibrium to be reached. The use of thinner samples or films is a partial solution to the heat transfer problem. However sample preparation becomes labor intensive and extremely time consuming since the sample must be machined to an exact thickness. Uniform thickness is often difficult to maintain and properties may be altered through the process of cutting and machining. Molded bars or parts which require minimal cutting remain the best choice for guaranteeing uniform thickness and unaltered properties.

The accuracy of DMA measurements depends largely on the attainment of thermal equilibrium at each measurement temperature. Some dynamic mechanical analyzers utilize a radiative oven similar to that in a conventional oven. Thermal energy is provided to the sample with heating elements that line the interior of the sample heating chamber. Heat transfer however with a relatively thick sample is poor for conditions under which temperature is continuously changing while measurements are made. There is little or no direct heat transfer in such units. Gas from a liquid nitrogen Dewar is circulated through the sample chamber. However, the gas normally enters the chamber outside an insulation barrier and very little convection directly onto the sample is created. At high temperatures nitrogen flow diminishes and heat transfer becomes purely radiative.

Other dynamic mechanical analyzers, on the other hand, employ forced convection, with heated or cooled gas blown directly into the sample chamber by way of for example a heat gun. Heat transfer is very efficient and thermal equilibrium is approached under most testing conditions. However, sufficient time is necessary for the entire sample to reach a uniform temperature before a measurement is made. This can be achieved using a step method whereby the temperature is increased incrementally and a specified equilibration time is allowed to elapse before obtaining each measurement. Drawbacks of this method are the long time required to complete a series of temperature steps and the limited accuracy which results from the use of temperature increments. Therefore uncertainties in transition temperatures exist. Total measurement time and accuracy of transitions are opposing factors with the step method. Smaller temperature increments improve accuracy but increase measurement time.

Suitable conditions for the step method can be implemented on certain commercially available devices. However, the typical testing time of six hours or more is impractical for large numbers of analyses. The efficient alternative to the step method is a temperature ramp, using a continuous, for example linear increase of temperature at a given rate.

Efficiency of analysis in the temperature ramp mode is much better than that of the step method if a fast heating rate is used. However, heat transfer becomes a severe limitation since the temperature of the sample lags behind the temperature of the surrounding gas. With an increasing temperature ramp, therefore, measured transitions are always different from the true values. Thermal lag within the sample can be minimized if effective heat transfer is provided and a reasonably slow ramp speed is employed.

When a temperature ramp is used under conditions of radiative heat transfer, significant thermal lag between the sample and oven temperatures is observed. The sample is actually being "baked" with the temperature of the interior always cooler than that of the surface. The most direct way to eliminate the thermal gradients within the sample is to use a step method instead of a temperature ramp. However, a significant drawback in this regard is that analysis times are undesirably long for the step method.

Another approach involves characterizing thermal lag in the temperature ramp mode for a given ramp speed and correcting the data by way of computer controls. Corrections can be made to the data using one or more points, however an assumption has to be made that the corrections for thermal lag are material independent, which may not be true if thermal conductivities vary.

Computer software provides the capability to implement corrections for thermal lag which occurs in a temperature ramp mode using devices which operate with radiative heat transfer The corrections can be made using either a single point, which results in simple subtraction of a specified value, or two points, which provides a linear variation of the correction over the entire temperature range. Experience in analyzing low and high temperature transitions on such instruments has shown that thermal lag varies significantly with temperature and therefore a two point correction is likely to be most effective. However, a linear relationship (independent of thermoplastic resin type and composition) is required for accurate and efficient implementation of the computer correction. Multiple corrections that depend on thermoplastic resin type are a possibility, but their utility becomes questionable for complex formulations.

Thermal lag in a temperature ramp mode was found to be very large at low temperatures but tended to decrease at high temperatures. There was not however a linear correlation of lag with temperature. While computer software correction of measured transition temperatures is better than no correction at all, the variability of thermal lag from one thermoplastic to another is a severe limitation.

Accordingly, there exists a need to improve the operation of DMAs which utilize radiative heat transfer, to provide for a more effective heat transfer to the material being tested.

SUMMARY OF THE INVENTION

It is a principal object of the invention to provide for a dynamic mechanical thermal analyzer (DMA) which provides for improved operation and testing ability.

It is a further object of the invention to provide for such a DMA which reduces the thermal lag, minimizes thermal deviation and avoids the need for expensive machining and preparation of the sample being tested.

A yet further object of the invention is to provide a method of improving such operation which may be readily incorporated in existing DMA devices that utilize radiative heat transfer.

Other objects will be further described below. The present invention is directed towards improving the speed of analysis provided by a dynamic mechanical analyzer by improving its heat transfer to the sample being tested. In the step mode the temperature within the sample being tested lags behind the actual oven temperature. This is particularly acute in DMA's that rely on radiative heat transfer with little or no gas circulation. The present invention is directed towards providing convective heat transfer in a DMA thereby reducing the temperature lag within a test sample. A device of the present invention comprises tubing bent into a desired configuration with numerous holes cut into the perimeter and placed at a specific location in the oven to direct gas flow unto the heating element. A gas such as nitrogen or air is supplied from an external source. The gas should be inert with respect to the sample, over the thermal test range. Nitrogen gas is preferred. The holes in the tubing allow the gas to flow outward over heating elements within the oven and not directly onto the sample. Forced convection heat transfer is obtained, and the temperature lag was found to be reduced from 20° C. or more to nothing or only a few degrees (0°-3° C.). If low temperature testing is needed a pre-mixing of external and cryogenic nitrogen streams can improve uniformity of oven temperatures.

The present invention is advantageous in that it may accommodate samples of various thickness while maintaining its improved operation and test results. Other advantages will be appreciated by the skilled artisan from the following description.

BRIEF DESCRIPTION OF THE DRAWING

Thus by the present invention, its objects and advantages will be realized, the description of which should be taken in conjunction with a viewing of the accompanying drawings, wherein:

FIG. 3 is a perspective view of a gas distribution device, incorporating the teachings of the present invention;

FIG. 4 is a sectional view of the oven cavity of the DMA showing the gas distribution device herein, incorporating the teachings of the present invention; FIGS. 5A and 5B are alternate perspective view of the gas distribution device, incorporating the teachings of the present invention.

DETAILED DESCRIPTION OF THE PREFERRED EMBODIMENTS OF THE INVENTION

Figure 1:
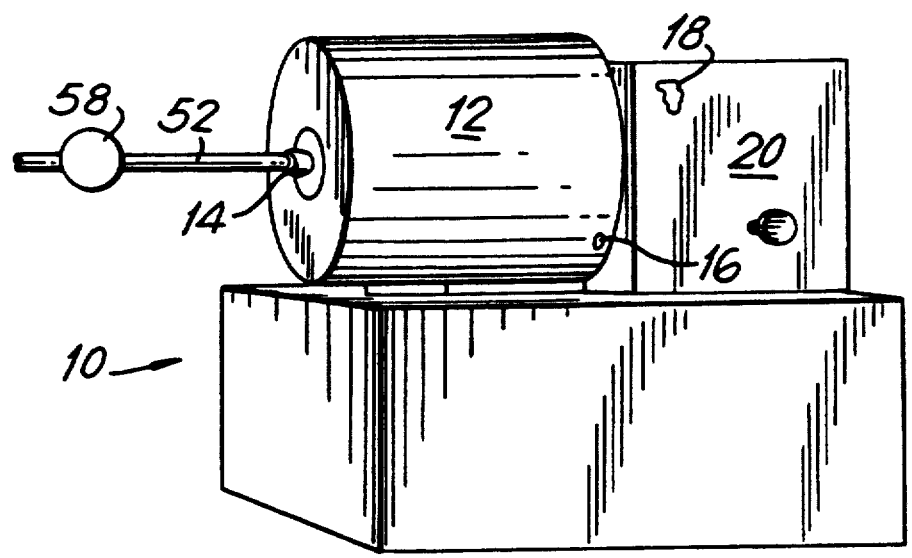
FIG. 1 is a perspective view of a dynamic mechanical analyzer, incorporating the teachings of the present invention.

Turning now more particularly to the drawings there is shown a dynamic mechanical analyzer (DMA) 10. The DMA 10 includes a cylindrical housing 12 which has therein a vacuum glass Dewar 13 (see FIG. 6), the end of which is shown at 14. Inside the Dewar 13, is a sample chamber or oven 15 (see FIGS. 4 and 6). A vent 16 is provided for the chamber along with an inlet port 18. Within the Dewar 13 and adjacent structure 20 is an electromechanical system 22 shown in FIG. 2. This system 22 includes an electromechanical driver 24 along with a linear variable displacement transducer 26 (with adjustment screw 28). Sample arms 30 are provided having a clamp 32 thereon to secure a sample 34. These arms 30 are coupled to flexure pivots 36 having arm locking pins 38, all of which is mounted on a mechanical slide 40.

A vernier adjustment mechanism 42 is provided along with a slide lock 44. Control and sample thermocouples are also provided and are generally illustrated at 46.

Within the sample chamber 15 is a series of heating elements 48 (shown most clearly in FIGS. 4 and 6) positioned within chamber opening 50 to provide radiative heating. As heretofore discussed, a problem with this design is the existence of thermal lag.

Normally to convert from radiative to convective heat transfer might involve installing a device inside the sample heating chamber to circulate the gas and provide better heat transfer. Installation of a small fan or blower inside the sample chamber is not possible due to small clearances and possible interference with the detection electronics. Two entry points for introduction of a gas from the outside are however available: one through the normal port 18 which is connected to a liquid nitrogen supply, and the second through the stoppered end 14 of the insulated glass Dewar 13.

The insertion of a small tube 52 through the end 14 of the glass Dewar 13 allows the penetration of the insulation barrier which surrounds the sample chamber 15. To avoid the difficulties of constructing a closed loop system for recirculating gas through a blower, nitrogen gas from an external supply, hereinafter referred to as "plant nitrogen", may be used at room temperature and introduced independently of the normal cryogenic gas stream.

To provide circulation, a gas distribution device 54 (see FIG. 3) is fabricated from ⅛" tubing (stainless steel) with 1mm diameter holes 56 drilled around the perimeter at 0.5 inch intervals. The device 54 is a manifold shaped in an oval adapted to reach the contours of a sample chamber 15 such as shown in FIG. 4. The holes are positioned such that the gas from the Dewar 13 will flow outward across the heating elements 48, as opposed to blowing directly onto the sample. Sufficient clearance is available for the tubing to lay against the bottom of the chamber without contacting the clamps 32. The plant nitrogen (and cryogenic gas stream if used) flow inside the Dewar 13 and exit through the vent 16. A flow meter 58 may be connected to the plant nitrogen line to allow monitoring of the gas flow rate.

To efficiently reach temperatures below −100° C. plant nitrogen flow rate can be controlled. Optimum conditions have been found at a flow rate of about 30 cubic feet/hoeur (CFH) but may be system dependent. Further refinement of the gas flow rate may be necessary to insure heating at a specified rate.

Figure 2:
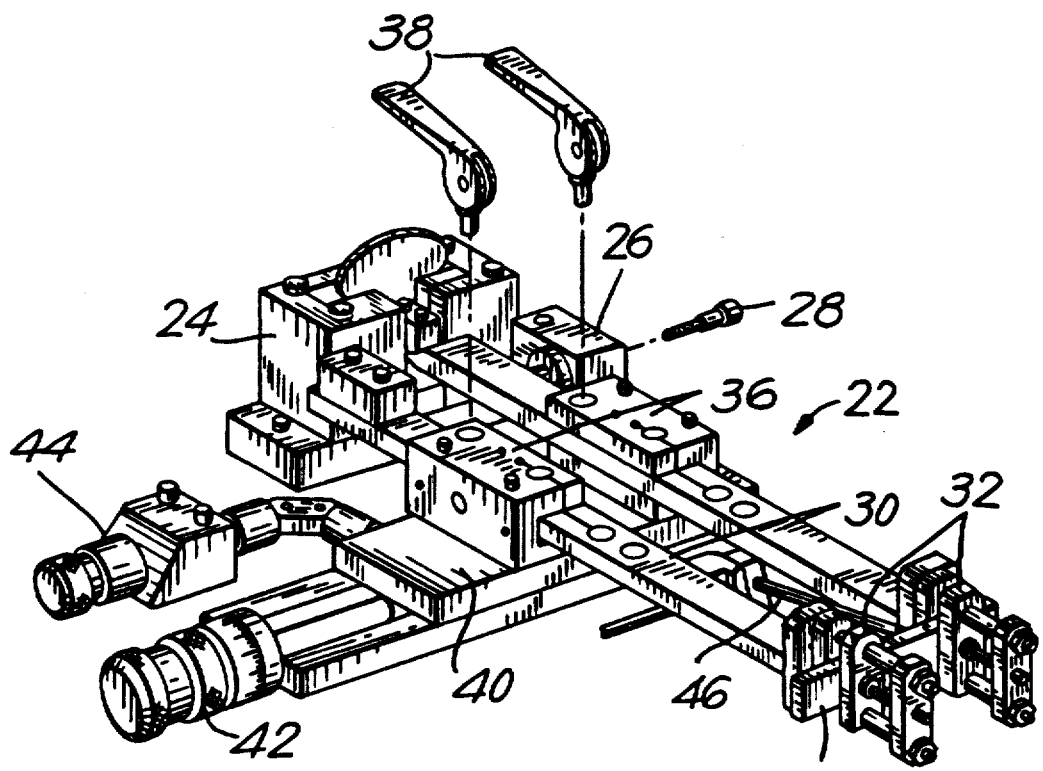
FIG. 2 is a perspective view of the electromechanical system of the dynamic mechanical analyzer of FIG. 1.

As shown in FIG. 2, thermocouple 46 is provided with a thermal lag device which is a sheath (stainless steel) which slides over the thermocouple 46 and shields it from gas currents. By utilizing this sheath device, a smooth response may be received from the thermocouple 46 and a further reduction in thermal lag is achieved.

Figure 6:
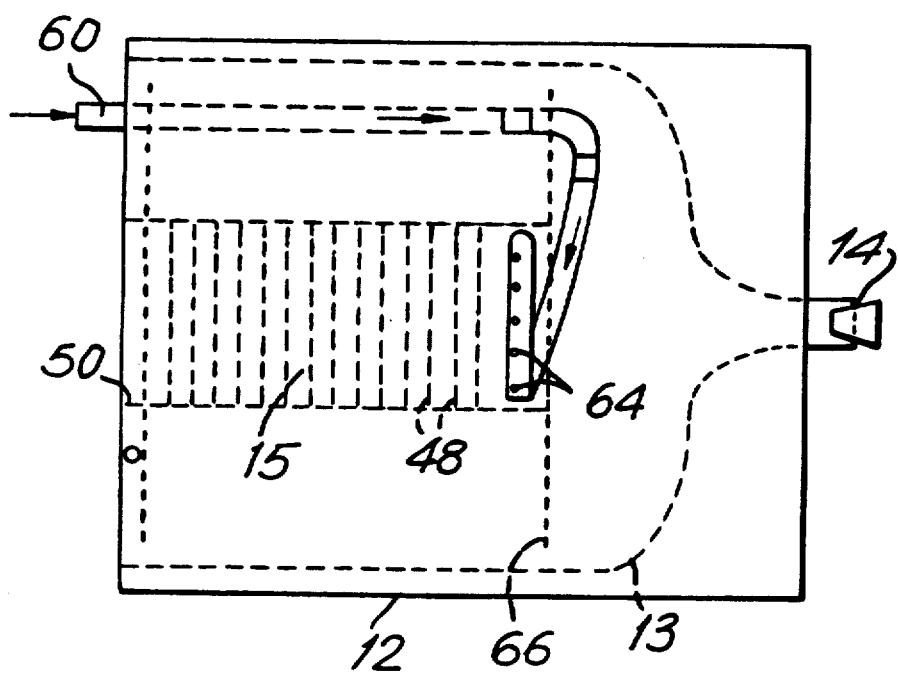
FIG. 6 is a side sectional, somewhat schematic view of the oven cavity, incorporating the teaching of the present invention.

In addition, rather than directing a separate gas stream through the end of the glass Dewar 13, the plant gas stream, (and cryogenic if used) can enter through the normal port 18 and the internal connection 60, shown in FIGS. 4–6. The housing 12 can be disassembled and a distribution device 62 (FIGS. 5A and 5B) can be connected internally. The new device 62 may be fabricated from ¼" tubing (such as copper tubing) with 1mm holes 64 spaced at ¼" intervals and positioned at an opening in the plate 66 located in the sample chamber 15. The holes 64 are drilled diagonally towards the chamber walls so that the gas blows across the heating elements and not directly on the sample. The geometry of the new tube 62 may be the same as that shown in FIG. 3 except that the connection may be made to the normal port 18. The external connection through the end of the Dewar 13 may then be eliminated.

The performance of this design is as follows. Temperature ramp speeds of three and four degrees Celsius per minute were compared and the results indicate slightly better accuracy at 3° C./min. An external nitrogen flow rate of 30 CFH was used. Cooling time at the start of an analysis was fast and equilibration time following tightening of the sample holding clamps was extremely short. The elimination of the external connection through the end of the glass Dewar 13 simplified handling of the sample chamber.

The invention having the internally connected gas distribution device 62 provided significant improvement in performance compared to the standard DMA, DuPont Model 983; E.I. Dupont DeNemours and Co., Wilmington, Delaware wherein no gas distribution device 62 was installed and nitrogen entered through port 18. (See the results set forth in Table A below). In this regard transition temperatures measured at 3° C./min. are shown for three cases: 1) radiative heat transfer with no corrections, 2) radiative heat transfer with software corrections for thermal lag, and 3) convective heat transfer using the internally connected distribution device. These results were compared to control data obtained on a Rheometrics dynamic spectrometer operating in a step mode. Temperature values in parentheses in Table A are deviations from the "control" data obtained in a step mode. The deviations therefore represent the measured thermal lag in the samples.

TABLE A

| | OVERALL IMPROVEMENTS TO THE DMA PERFORMANCE | | | |
|---|---|---|---|---|
| | | TRANSITION TEMPERATURES (C.°) | | |
| Thermoplastic Material | Control | 1. 3° C./min. Normal Operation (Unmodified DMA) | 2. 3° C./min Software Corrections | 3. DMA of the Invention 3° C./min. |
| I. VALOX ® 295 | 58.9 (1° C./step) | 80.0 (18.4) | 63.2 (4.3) | 57.6 (−1.3) |
| II. LOMOD ® A1320 | −76, −41, 58 (4° C./step) | −57.1, −21.7, 78.5 (18.9, 19.3, 20.5) | −79.6, −41.2, 62.2 (−3.6, −0.2, 4.2) | −75.4, −41.5, 56.9, (0.6, −0.5, 1.1) |
| III. XENOY ® 1102 | −83.5, 70, 134 (4° C./step) | −59.4, 87.2, 148.6 (24.1, 17.2, 14.6) | −84.8, 71.9, 135.9 (−1.3, 1.9, 1.9) | −81.4, 131 (2.1, −3.0) |
| IV. LEXAN ® 140 | −96.7, 156.5 (4° C./step) | −70.4, 165.3 (26.3, 8.8) | −94.3, 152.3 (2.4, −4.2) | −94.5 (2.2) |

I. Polybutylene terephthalate, General Electric Co.
II. Polyether polyester, General Electric Co.,
III. An admixture of Polycarbonate, Polybutylene terephthalate and a rubber, General Electric Company
IV. Polycarbonate Resin, General Electric Company The data show that convective heat transfer is a highly effective method for improving accuracy. Numerically, it compares favorably with the expensive software method of correcting data. Convective heat transfer is, however, superior because it does not involve artificial manipulation of data and no assumptions need to be made regarding thermal conductivity.

The modification of the DMA to produce convective heat transfer improves instrument performance. The so modified device has lower operating costs, faster turnaround times and lesser initial investment since the software correction capability is no longer necessary.

Thus by the present invention, its objects and advantages are realized, and although a preferred embodiment has been disclosed and described in detail herein, its scope should not be limited thereby. Rather its scope should be determined by that of the appended claims.

What is claimed is:

1. A dynamic mechanical analyzer device for use in measuring mechanical and rheological properties of samples of thermoplastic materials in a solid state as a function of temperature over a constantly changing temperature profile, comprising;
   a sample chamber in which a sample of the material is to be tested;
   said sample chamber comprises a means of providing radiative heating to the sample;
   convective transfer means in said sample chamber for supplying a flow of a first gas across the radiative heating means wherein said gas is heated by said heating means to cause a forced convection heat transfer to said sample;
   said convective heat transfer means includes conduit means having a series of openings positioned adjacent the radiative heating means; and
   wherein through the use of the convective transfer means, temperature lag as between the chamber temperature and that of the sample is diminished.

2. The device in accordance with claim 1 which further includes means for providing cryogenic gas and combining said cryogenic gas with the first gas in the convective transfer means and supplying said combined gases to the sample chamber.

3. The device in accordance with claim 1 wherein said convective transfer means generates a gas flow in the sample chamber.

4. The device in accordance with claim 3 wherein said gas does not directly impinge upon the sample.

5. A dynamic mechanical analyzer device for use in measuring mechanical and rheological properties of samples of thermoplastic materials in a solid state as a function of temperature comprising;
   a sample chamber in which a sample of the material is to be tested;
   said sample chamber comprises a means of providing radiative heating to the sample;
   convective transfer means in said sample chamber for generating a flow of a first gas in the sample chamber across the radiative heating means;
   said convective transfer means includes conduit means having a series of openings positioned adjacent the radiative heating means, said gas is heated by said heating means to cause a forced convection heat transfer to said sample without having the gas directly impinging upon the sample; and
   wherein through the use of the convective transfer means, temperature lag as between the chamber temperature and that of the sample is diminished.

6. The device in accordance with claim 5 wherein said conduit means is a closed tubular member which is coupled to a source of the first gas.

7. The device in accordance with claim 5 wherein said series of openings are located in the sample chamber, away from the sample, and are so formed so as to cause the gases to pass over the radiative heating means.

* * * * *